US 8,768,451 B2
United States Patent
Atanasoska et al.

(10) Patent No.: US 8,768,451 B2
(45) Date of Patent: Jul. 1, 2014

(54) THERAPEUTIC AGENT DELIVERY DEVICE FOR DELIVERY OF A NEUROTOXIN

(75) Inventors: Liliana Atanasoska, Edina, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 347 days.

(21) Appl. No.: 13/096,492

(22) Filed: Apr. 28, 2011

(65) Prior Publication Data

US 2011/0270152 A1 Nov. 3, 2011

Related U.S. Application Data

(60) Provisional application No. 61/330,201, filed on Apr. 30, 2010.

(51) Int. Cl.
*A61N 1/30* (2006.01)

(52) U.S. Cl.
USPC ............................................. 604/20; 604/501

(58) Field of Classification Search
USPC ............. 604/20–26, 500–510, 96.01, 164.01, 604/523
See application file for complete search history.

(56) References Cited

U.S. PATENT DOCUMENTS

| 6,210,392 | B1 | 4/2001 | Vigil et al. |
| 6,579,847 | B1 | 6/2003 | Unger |
| 6,592,617 | B2 | 7/2003 | Thompson |
| 6,767,544 | B2 | 7/2004 | Brooks et al. |
| 7,850,645 | B2 | 12/2010 | Atanasoska et al. |
| 2003/0211975 | A1 | 11/2003 | Unger |
| 2004/0223975 | A1* | 11/2004 | Brooks et al. ............... 424/184.1 |
| 2007/0208365 | A1 | 9/2007 | Lee et al. |
| 2007/0208405 | A1 | 9/2007 | Goodin et al. |
| 2008/0004596 | A1 | 1/2008 | Yun et al. |
| 2008/0107794 | A1 | 5/2008 | O'Connor et al. |
| 2008/0262412 | A1* | 10/2008 | Atanasoska et al. ............ 604/20 |

FOREIGN PATENT DOCUMENTS

| WO | 99/04851 A1 | 2/1999 |
| WO | 2007/046103 A2 | 4/2007 |

OTHER PUBLICATIONS

Buoninsegni, Francesco Tadini, et al., "Total and free charge densities on mercury coated with self-assembled phosphatidylcholine and octadecanethiol monolayers and octadecanethiol/phosphatidylcholine bilayers," Journal of Electroanalytical Chemistry, vol. 500, pp. 395-407 (2001).

Cosnier, S., et al., "Fabrication of biosensors by attachment of biological macromolecules to electropolymerized conducting films," Analusis, vol. 27, No. 7, pp. 558-564 (1999).

(Continued)

*Primary Examiner* — Kevin C Sirmons
*Assistant Examiner* — Phillip Gray
(74) *Attorney, Agent, or Firm* — Kenyon & Kenyon LLP

(57) ABSTRACT

A therapeutic agent delivery device and method for eluting a therapeutic agent to a target location are disclosed. The therapeutic agent delivery device may comprise a first conductive element, a second conductive element, and an electrochemical layer including a neurotoxin located between the first conductive element and the second conductive element. The first conductive element and the second conductive element are adapted to be connected to a voltage source. When the first conductive element and the second conductive element are connected to the voltage source, an electrochemical reaction occurs causing the neurotoxin to release from the electroactive layer and elute to a target location.

13 Claims, 4 Drawing Sheets

(56) References Cited

OTHER PUBLICATIONS

Cosnier, Serge, et al., "Poly(pyrrole-biotin): a new polymer for biomolecule grafting on electrode surfaces," Electrochimica Acta, vol. 44, pp. 1833-1836 (1999).

Daniels-Holgate, P.U., et al., "Productive and Non-Productive Binding of Botulinum Neurotoxin A to Motor Nerve Endings Are Distinguished by Its Heavy Chain," Journal of Neuroscience Research, vol. 44, pp. 263-271 (1996).

Da Silva, S., et al., "Biotinylated polypyrrole films: an easy electrochemical approach for the reagentless immobilization of bacteria on electrode surfaces," Bioelectrochemistry, vol. 63, pp. 297-301 (2004).
Dean, David A., "Electroporation of the Vasculature and the Lung," DNA and Cell Biology, vol. 22, No. 12, pp. 797-806 (2003).
Duncan, Ruth, "The Dawning Era of Polymer Therapeutics," Nature Reviews, vol. 2, pp. 347-360 (2003).
Dupont-Filliard, A., et al., "Comparison by QCM and photometric enzymatic test of the biotin-avidin recognition on a biotinylated polypyrrole," Talanta, vol. 55, pp. 981-992 (2001).
Dupont-Filliard, A., et al., "Reversible ologonucleotide immobilisation based on biotinylated polypyrrole film," Analytica Chimica Acta, vol. 449, pp. 45-50 (2001).
Gooding, J. Justin, et al., "Electrochemical modulation of antigen-antibody binding," Biosensors and Bioelectronics, vol. 20, pp. 260-268 (2004).
Lavasanifar, Afsaneh, et al., "Poly(ethylene oxide)-block-poly(L-amino acid) micelles for drug delivery," Advanced Drug Delivery Reviews, vol. 54, pp. 169-190 (2002).
Ozoemena, Kenneth, et al., "Voltammetric characterization of the self-assembled monolayer (SAM) of octabutylthiophthalocyaninatoiron(II): a potential electrochemical sensor," Electrochimica Acta, vol. 47, pp. 4035-4043 (2002).
Wackerbarth, Hainer, et al., "Thiol- and disulfide-modified oligonucleotide monolayer structures on polycrystalline and single-crystal Au(111) surfaces," Journal of Solid State Electrochemistry, vol. 8, pp. 474-481 (2004).
Wrobel, Nadia, et al., "Covalent immobilization of oligonucleotides on electrodes," Colloids and Surfaces B: Biointerfaces, vol. 32, pp. 157-162 (2003).
Yang, Xiaoming, MD, PhD, "Imaging of Vascular Gene Therapy," Radiology, vol. 228, No. 1, pp. 36-49 (2003).
International Search Report and the Written Opinion of the International Searching Authority, or the Declaration, mailed Aug. 24, 2011, from related International Application No. PCT/US2011/034306.

* cited by examiner a charged therapeutic agent in the direction of an internal electrode). Voltage may be applied to release the therapeutic agent (e.g., via iontophoresis of a charged therapeutic agent in the direction of an electrode that is external to the therapeutic agent source, or via neutralization of a conductive polymer which leads to expulsion of a charged therapeutic agent from the device). The voltage also may be applied to promote electroporation.

THERAPEUTIC AGENT DELIVERY DEVICE FOR DELIVERY OF A NEUROTOXIN

CROSS REFERENCE TO RELATED APPLICATION

The present application claims priority to U.S. provisional application Ser. No. 61/330,201 filed Apr. 30, 2010, the disclosure of which is incorporated herein by reference in its entirety.

FIELD OF THE INVENTION

The present invention relates to the delivery of therapeutic agent, for example to the interior walls of a vessel such as a blood vessel, via a therapeutic agent delivery device.

BACKGROUND INFORMATION

Internal medical devices for delivery of therapeutic agents in conjunction with a source of electrical power is the subject of co-pending U.S. patent application Ser. No. 12/077,603 (published as U.S. Patent Application Publication No. 2008/0262412) to Atanasoska et al. (hereinafter "the '603 application"), filed Mar. 20, 2008, which is a continuation of U.S. patent application Ser. No. 11/055,930 (now U.S. Pat. No. 7,850,645). These applications describe processes for delivering a therapeutic agent to a location within a blood vessel. The disclosures of these applications are expressly incorporated herein by reference.

The '603 application describes devices for delivery of therapeutic agents to a diseased location based on electric field effects (i.e., delivery is electrically assisted), such as iontophoresis, electroporation, or both. The '603 application generally relates to internal drug delivery devices which contain a source of therapeutic agents, electrodes and power sources for applying voltages across the first and second electrodes. The power sources may be adapted, for example, to promote electrically assisted therapeutic agent delivery within a subject, including electroporation and/or iontophoresis. The therapeutic agent sources are polymeric regions that contain one or more types of electrically conductive polymers and one or more types of charged therapeutic agents or are polymeric regions that contain one or more types of ion-conductive polymers and one or more types of charged therapeutic agents. By placing the therapeutic agent within a polymer region, movement of the therapeutic agent is restricted and thus more precise local dosing of the therapeutic agent is possible. This design is also advantageous in that it allows one to provide different therapeutic agents or different therapeutic agent dosages for different sections of the device, which can be beneficial in various instances (e.g., where vulnerable plaque is located on one side of a vessel).

Iontophoresis is an electrochemical process by which an electric field is used as a driving force to move a drug into a subject. This technique typically requires two or more electrodes for creating an electric field as well as a drug that carries a net electrical charge at the local physiological pH.

Electroporation methods use short, high-voltage pulses to create transient pores in the cell membranes or in organelles within the cells. This transient, permeabilized state can be used to load cells and organelles with a wide variety of therapeutic agents, for example, genes, proteins, small molecule drugs, dyes, tracers, and so forth.

Voltage may be applied to at least temporarily retain the therapeutic agent within the device (e.g., via iontophoresis of a charged therapeutic agent in the direction of an internal electrode). Voltage may be applied to release the therapeutic agent (e.g., via iontophoresis of a charged therapeutic agent in the direction of an electrode that is external to the therapeutic agent source, or via neutralization of a conductive polymer which leads to expulsion of a charged therapeutic agent from the device). The voltage also may be applied to promote electroporation.

Iontophoretic retention and release can be induced by application of a variety of electrical stimuli including: (a) constant current, (b) constant voltage, (c) current scan/sweep, e.g., via a single sweep or multiple sweeps, (d) voltage scan/sweep, e.g., via a single sweep or multiple sweeps, (e) current square waves or other current pulse wave forms, (f) voltage square waves or other voltage pulse wave forms including exponential voltage output pulses, and (g) a combination of different current and voltage parameters.

For electroporation, high voltage pulses are generally used to create the transient pores within cells exposed to the electric field, allowing the cells to be loaded with therapeutic agent (e.g., due to diffusion, migration or both). The density and size of the transient open pores of the cell membrane depend, for example, on the electric field parameters and polarity. This can be used to tailor the entry of various therapeutic agents of various sizes into the cell membranes or into organelles within the cells.

The '603 application describes electrodes adapted to have tissues of a subject positioned between them upon deployment of the medical device within the subject, such that an electric field may be generated, which has a vector that is directed into the tissue. Furthermore, the therapeutic agent sources are adapted to introduce the one or more therapeutic agents into the as-generated electric field. This may result, for example, in increased electroporation efficiency, increased iontophoresis efficiency (e.g., where one or more charged therapeutic agents are employed), or both.

The '603 application also describes ion-conductive polymeric regions, which are polymeric regions that permit movement of ions and the movement of charged therapeutic agents. Like other ionic species, charged therapeutic agents move in response to concentration gradients and in response to electric fields. In addition to allowing ion movement, ion-conductive polymeric regions are also capable of maintaining therapeutic agents in an ionized form, as opposed to a charge-neutral form. Charge-neutral species are generally not transported in response to an electric field. Polymers suitable for maintaining therapeutic agents in ionized form commonly have cation and/or anion coordinating sites, which are capable of forming complexes with ions, or they are themselves ionized. Polyelectrolytes may be employed as ion conductive polymers. Polyelectrolytes are polymers having multiple (e.g., 5, 10, 25, 50, 100, or more) charged sites (e.g., ionically dissociable groups).

The '603 application also describes conductive polymers, such as polypyrrole. Conductive polymers commonly feature a conjugated backbone (e.g., a backbone containing an alternating series of single and double carbon-carbon bonds). Conductive polymers are typically semi-conductors in their neutral state. However, upon oxidation or reduction of the polymer to a charged state (e.g., polypyrrole is positively charged when oxidized and is neutral when reduced), the electrical conductivity is understood to be changed from a semi-conductive regime to a semi-metallic regime. Oxidation and reduction are believed to lead to charge imbalances that, in turn, can result in a flow of ions into or out of the material. These ions typically enter/exit the material from/into an ionically conductive medium associated with the polymer. For example, it is well known that dimensional changes are effectuated in electroactive polymers, including conductive polymers, by the mass transfer of the ions (which are surrounded by a shell of water molecules) into or out of the polymers. The mass transfer of ions into and out of the material leads to an expansion or contraction of the polymer, delivering significant stresses (e.g., on the order of 1 MPa) and strains (e.g., on the order of 30%).

The fact that oxidation and reduction of conductive polymers is associated with the flow of ions into or out of the material makes these materials useful for retention and/or delivery of charged therapeutic agents. The properties of polypyrroles and other conductive polymers allow them to provide a mechanical component to the therapy, making them particularly desirable for delivery of charged therapeutic agents, for example, in conjunction with electroporation procedures.

SUMMARY OF THE INVENTION

The invention is directed to improvements in devices and methods for delivery of a therapeutic agent to a target location, such as the inside of a vessel. In particular, the invention is directed to devices and methods for delivery of a neurotoxin to a target location, such as the inside of a vessel.

In an embodiment of the invention, a method of delivering a therapeutic agent to a target location is provided. The method comprises providing a therapeutic agent delivery device comprising a conductive element and a neurotoxin, wherein the conductive element is adapted to be connected to a voltage source. The method further comprises positioning the therapeutic agent delivery area of the device at a target location and connecting the conductive element to the voltage source, thereby causing the neurotoxin to release from the electroactive layer and elute to a target location.

In a further embodiment of the invention, a therapeutic agent delivery device is provided comprising a first conductive element, a second conductive element, and an electrochemical layer including a neurotoxin located between the first conductive element and the second conductive element. The first conductive element and the second conductive element are adapted to be connected to a voltage source. In this embodiment, when the first conductive element and the second conductive element are connected to the voltage source, an electrochemical reaction occurs causing the neurotoxin to release from the electroactive layer and elute to a target location.

A disclosed further embodiment provides for a therapeutic agent delivery device in which the electroactive layer further comprises an electroactive polymer matrix, a first linking element adapted to bind to the electroactive polymer matrix, a second linking element adapted to bind to the neurotoxin, and a bridging element. In this embodiment, the bridging element is adapted to form a first bond to the first linking element and a second bond to the second linking element simultaneously, thereby forming a bridge to connect the electroactive polymer matrix and the neurotoxin. In this embodiment, when the electrode regions are connected to the voltage source, a current may sever the first bond and/or the second bond and compel iontophoretic transfer of the neurotoxin to the target location. In this embodiment, the current may further cause electroporation of a membrane of the target location to enhance delivery of the neurotoxin into target tissues.

In a further embodiment, the neurotoxin forms a self-assembled monolayer on a surface of at least one of the first conductive element and the second conductive element. In this embodiment, when the electrode regions are connected to the voltage source, a current transfers the neurotoxin into the target location by reductive desorption. In this embodiment, the current may further cause electroporation of a membrane of the target location to enhance delivery of the neurotoxin into target tissues.

Depending on the embodiment, the invention can have advantages including reduced loss of therapeutic agent during and/or after the procedure, simplicity of design, reduced procedural complications, improved ease of use, and/or improved overall performance during and/or after the procedure. These and other features and advantages of the disclosed devices and methods are described in, or apparent from, the following detailed description of various exemplary embodiments.

BRIEF DESCRIPTION OF THE DRAWINGS

Various embodiments will be understood more readily through the following detailed description, with reference to the accompanying drawings, in which.

DETAILED DESCRIPTION

Figure 1:
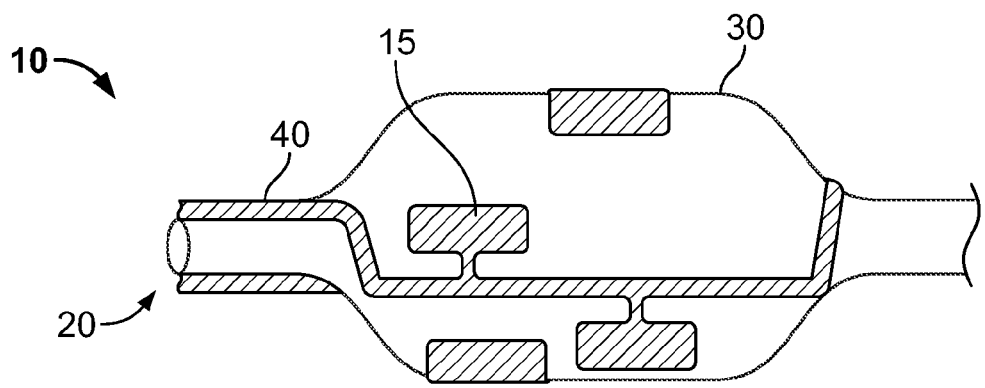
FIG. 1 is a perspective view of a therapeutic agent delivery device of the present invention.

For a general understanding of the features of the illustrated embodiments of the invention, reference is made to the drawings. In the drawings, like reference numerals have been used throughout to designate like elements.

As illustrated in FIG. 1, a therapeutic agent delivery device 10 according to a first embodiment includes electrical leads 40 engaged to electrode regions 15 located on an expandable member 30. The electrode regions 15 may be applied by any suitable method such as, for example, sputter deposition. The expandable member 30 may be mounted on the distal end of a catheter 20 for delivery to a desired target location such as, for example, within the vasculature of the human body. The electrode regions 15 may be situated on an outer surface of the expandable member 30 in any suitable configuration. The electrical leads 40 may be connected to a voltage source (not shown).

Expandable member 30 may be any suitable device capable of being expanded in a radial direction. In its unexpanded position (not shown), the diameter of the expandable member 30 should be such that the catheter 20 and the expandable member 30 move easily throughout the delivery passage, e.g., the vascular system, without causing damage to the tissue. In its expanded position, as illustrated in FIG. 1, the expandable member 30 expands radially to approach the inner surface of the lumen or vessel, i.e., the vessel wall, such that the electrode regions 15 are in contact with the lumen wall or tissue or blood adjacent to and inside the lumen.

In embodiments, such as those shown in FIG. 1, the expandable member 30 may be a balloon. Any suitable material may be used for the balloon 30, such as, for example, a polymeric material. Angioplasty balloon materials have been the subject of a number of patents and patent applications including U.S. Patent Application Publication No. 2007/0208365 to Lee et al. and U.S. Patent Application Publication No. 2007/0208405 to Goodin et al. The disclosures of these applications are expressly incorporated herein by reference. The balloon 30 may be formed, for example, from a high durometer PEBAX®, such as PEBAX® 7233, 7033 or 6333 or NYLON 12®.

Examples of other polymeric materials that the balloon 30, or layers of the balloon 30, may be formed from include polyethylene, HYTREL®, polyester, polyurethane, ABS (acrylonitrile-butadiene-styrene) block copolymer, ABS/Nylon blends, ABS/polycarbonate blends and combinations thereof, styrene-acrylonitrile block copolymers, other acrylonitrile copolymers, polyacrylamide, polyacrylates, polyacrylsulfones, polyester/polycaprolactone blends, polyetheretherketone (PEEK), polyethersulfone (PES), polyetherimide (PEI), polyetherketone (PEK), polymethylpentene, polyphenylene ether, polyphenylene sulfide, polyolefins such as polyethylene and polypropylene, olefin copolymers, such as ethylene-propylene copolymer, ethylene-vinyl acetate copolymers, ethylene-vinyl alcohol copolymers and polyolefin ionomers, polyvinyl chloride, polycaprolactam, N-vinyl-pyrrolidone, polyurethanes and polysiloxanes.

The electrical leads 40 may be comprised of any suitable conductive material such as, as just one of many possible examples, a cobalt-based alloy. Conductive materials have been the subject of a number of patents including commonly assigned U.S. Pat. No. 6,592,617 to Thompson. The disclosure of this patent is expressly incorporated herein by reference. In embodiments, the electrical lead 40 may be formed from 316 L stainless steel or a MP35N alloy. Examples of other materials from which electrical lead 40 may be formed are sold under the brand names Elgiloy® and Phynox®. Other metallic materials that may be used include Nitinol nickel-titanium. The electrical lead 40 may also be a wire or strand, such as a polyolefin fiber, coated with conductive material.

As illustrated in FIGS. 2A-2D, electrode regions 15 may comprise a first conductive element 16 and a second conductive element 17. Conductive elements 16, 17 may be configured in any suitable manner around the outer surface of the expandable member 30. In this embodiment, an electrochemical layer 50 is located between the first conductive element 16 and the second conductive element 17. The electrochemical layer 50 completes an electrical circuit between the first conductive element 16 and the second conductive element 17 via elements contained in the electrochemical layer 50 that act as an electrolyte.

In certain embodiments, the first and second conductive elements 16, 17 may comprise Au, Ag, Pd, Pt, Fe, Mg or any suitable alloy thereof. Any suitable metal or metal alloy or conductive non-metal material is within the scope and spirit of this invention.

Figure 2A:
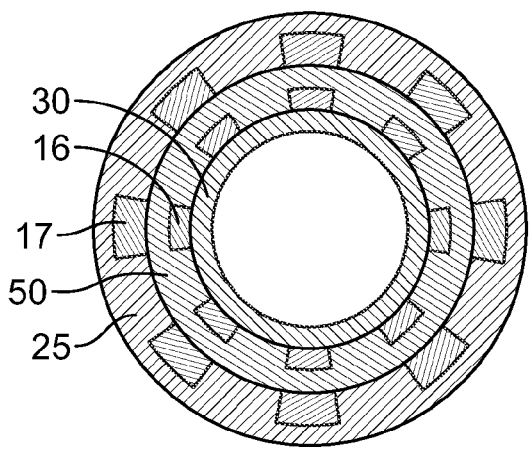
FIG. 2A is a schematic cross-sectional view of the therapeutic agent delivery device illustrated in FIG. 1, in accordance with an embodiment of the present invention.
Figure 2B:
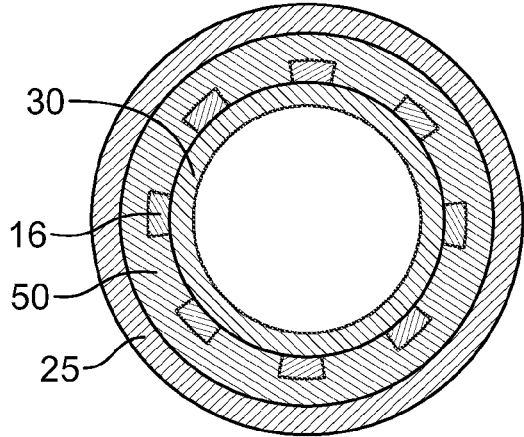
FIG. 2B is a schematic cross-sectional view of the therapeutic agent delivery device illustrated in FIG. 1, in accordance with another embodiment of the present invention.
Figure 2C:
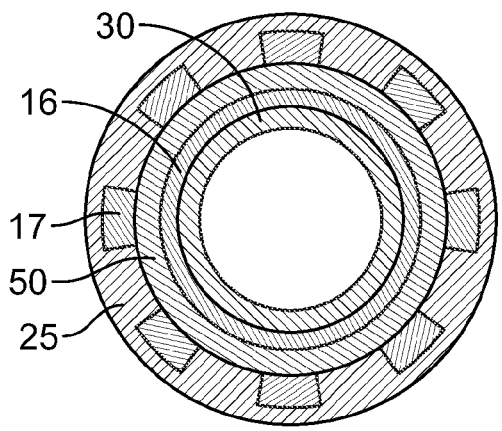
FIG. 2C is a schematic cross-sectional view of the therapeutic agent delivery device illustrated in FIG. 1, in accordance with another embodiment of the present invention.
Figure 2D:
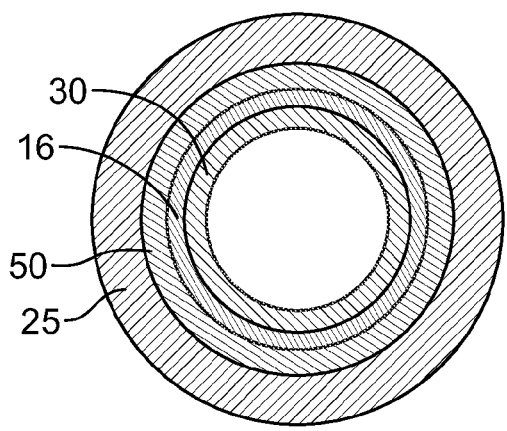
FIG. 2D is a schematic cross-sectional view of the therapeutic agent delivery device illustrated in FIG. 1, in accordance with another embodiment of the present invention.

FIGS. 2A-2D show various suitable configurations according to different embodiments. As illustrated in FIG. 2A, first conductive element(s) 16 is disposed on the outer surface of the expandable member 30. The electrochemical layer 50 is applied over the first conductive element(s) 16. Second conductive element(s) 17 is provided on the outer surface of the electrochemical layer 50. FIG. 2B depicts another embodiment in which only the first conductive element(s) 16 is applied on the outer surface of the balloon. In this embodiment, the second conductive element(s) is/are applied outside the lumen, such as, for example, on the skin of the patient. FIG. 2C depicts another embodiment in which the first conductive element 16 is continuously applied around the outer surface of the expandable member 30. FIG. 2D depicts yet another embodiment in which the first conductive element 16 is continuously applied around the outer surface of the expandable member 30 and only the first conductive element(s) 16 is applied on the outer surface of the balloon. In the embodiments of FIGS. 2B and 2D, tissue or target location 25 acts as the electrolyte carrying charge to complete the electrical circuit, as would be understood by one of ordinary skill in the art.

The target location 25 in this embodiment may be, for example, blood, an inner wall of a blood vessel, human tissue or any combination thereof. The vessel may be any vessel located within or outside of the body of a patient and suitable for use with the invention. It may include blood-carrying vessels such as the veins, arteries, and chambers of the heart; it may also include the esophagus, the ureters, the intestines, the pockets of fluid located within the individual vertebrae of the spinal column and any other suitable vessel as apparent to one of skill in the art. Organs and tissues that may be treated by the present invention include any mammalian tissue or organ, whether located in vivo or ex vivo. Non-limiting examples include the vasculature of the heart, the lungs, the brain, the livers, the kidneys, the bladder, the intestines, the stomach, and the pancreas.

Figure 3:
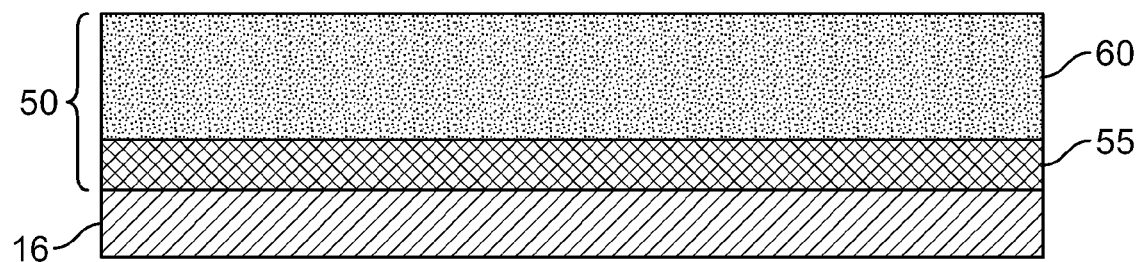
FIG. 3 is a cross-sectional view of an electrode region of the therapeutic agent delivery device illustrated in FIG. 1 according to the first embodiment.

As illustrated in FIG. 3, the electrochemical layer 50 located between the first conductive element 16 and the second conductive element 17 is adapted to at least partially coat the first conductive element 16. The electrochemical layer 50 may include a neurotoxin 60. Neurotoxins are generally "toxic" to the human nervous system. However, the use of neurotoxins in alternative medical procedures, such as, for example, cosmetic surgery, are well known. It is an object of the present invention to apply the toxicity of neurotoxins in an unexpectedly beneficial manner to the vasculature of the human body. In effect, these toxins prevent elastic recoil and/or restenosis and maintain the opening of a vessel by causing a paralysis of the vessel.

Figure 4:
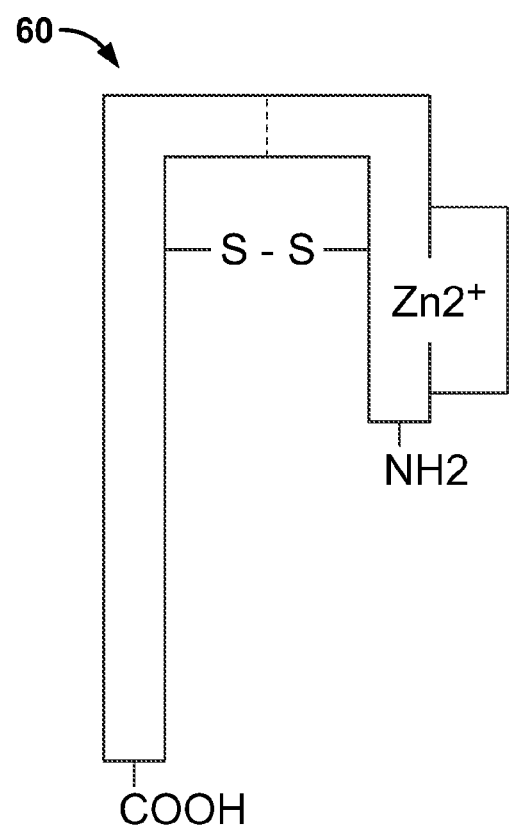
FIG. 4 is a schematic view of a neurotoxin according to the first embodiment.

As illustrated in FIG. 4, the neurotoxin 60 may comprise botulunim toxin (A-G) in accordance with the first embodiment. The neurotoxin may also comprise the botulunim toxin producing bacteria Clostridium botulinum. Botulinum toxin attaches to nerve endings causing paralysis. Botulinum toxin's toxicity is derived from its ability to attack a series of proteins, VAMP, syntaxin and SNAP-25, that are responsible for the release of acetylcholine. Once attached, acetylcholine, the neurotransmitter responsible for triggering muscle contractions, cannot be released. Botulinum toxin, in particular, causes paralysis in involuntary muscles such as organs and vasculature. In the case of a blood vessel, a neurotoxin such as botulinum toxin can cause a flaccid paralysis in the vascular smooth muscle tissue, which can help prevent or reduce elastic recoil and/or restenosis. The effects of botulinum toxin are well documented and described in, for example, Daniels-Holgate et al., "Productive and non-productive binding of botulinum neurotoxin A to motor nerve endings are distinguished by its heavy chain," Journal of Neuroscience Research, Vol. 44, Issue 3, pp. 263-271 (1996).

Additionally, the neurotoxin may be charged or have charging sites that facilitate iontophoretic transfer and electroporation described herein, as described in the '603 application and as would be understood by one of ordinary skill in the art. Any suitable toxin capable of, or useful in, preventing elastic recoil of the lumen after disengagement of the expandable member 30 from the inner surface of the lumen or vessel 25, including derivatives and analogs of botulinum toxin, is within the scope and spirit of this invention.

The electrochemical layer 50 may also comprise an electroactive polymer matrix 55. Because the expandable member 30 is generally not conductive, growing an electroactive polymer matrix 55 on a surface of the electrode regions 15 disposed on the outer surface of the expandable member 30 is more effective, as would be understood by one of ordinary skill in the art.

Electroactive polymers are members of a family of plastics referred to as "conducting polymers." They are a class of polymers characterized by their ability to change shape in response to electrical stimulation. They expand and contract upon application of an appropriate electrical potential. They typically structurally feature a conjugated backbone and have the ability to increase electrical conductivity under oxidation or reduction. In embodiments, the electroactive polymer is polypyrrole. Polypyrrole exhibits superior stability under physiological conditions. The structure of polypyrrole is depicted below:

Known derivatives of polypyrrole include the following substituted polymers: poly(N-methylpyrrole), poly(N-butylpyrrole), poly[N-(2-cyanoethyl)pyrrole], poly[N-(2-carboxyethyl)pyrrole], poly(N-phenylpyrrole), poly[N(6-hydroxyhexyl)pyrrole], and poly[N-(6-tetrahydropyranylhexyl)pyrrole], among others. In addition to polypyrrole, any conducting polymer, including analogs of polypyrrole, that exhibits suitable contractile or expansile properties may be used within the scope of the invention.

Figure 5:
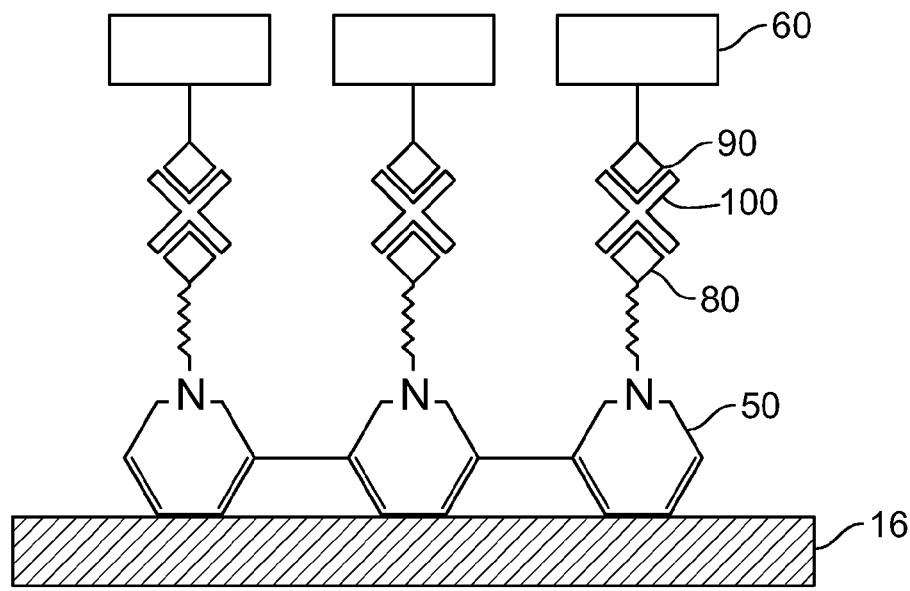
FIG. 5 is a schematic view of an electroactive layer of the therapeutic agent delivery according to the first embodiment.

As illustrated in FIG. 5, the electrochemical layer 50 also may comprise means for immobilizing the neurotoxin 60 on the electroactive polymer matrix 55. Immobilization techniques are well known in the art. It is an object of the present invention to immobilize the neurotoxin 60 on the outer surface of the expandable member 30 and control release of neurotoxin 60 at the desired time. Additionally, the advantages of using an electropolymerizable pyrrole polymer modified with biotin for immobilizing biomolecules is well documented. See, for example, Cosnier et al., "Poly(pyrrole-biotin): a new polymer for biomolecule grafting on electrode surfaces," Electrochimica Acta, Vol. 44, pp. 1833-1836 (1999). It is further well documented that biomolecules may, themselves, be modified with biotin. See, for example, Da Silva et al., "Biotinylated polypyrrole films: an easy electrochemical approach for the reagentless immobilization of bacteria on electrode surfaces," Bioelectrochemistry, Vol. 63, pp. 297-301 (2004). These publications are expressly incorporated herein by reference.

It is believed that immobilization of biomolecules in an electropolymerizable matrix occurs due to electrostatic interactions between negatively or prohibitively charged proteins and polymer films. Such interactions, however, may cause the immobilized protein to be "trapped" or substantially altered. To overcome this deficiency, chemical grafting has been considered. Chemical grafting, in effect, functionalizes the polymer layer. The present invention provides for such a functionalization.

As illustrated in FIG. 5, the electroactive layer 50 also may comprise a first linking element 80 adapted to bind to the electroactive polymer matrix 55. In embodiments, the linking element 80 may comprise biotin. The structure of biotin is as depicted below:

In the above depiction, R represents a functional group. In embodiments, R is the electropolymer matrix 55 constituent. By binding the biotin molecule to polypyrrole the electropolymer matrix 55 is functionalized. When this process involves the use of biotin, it is referred to as biotinylation. A resulting representative structure of a biotinylated polypyrrole is:

(1)

Figure 6:
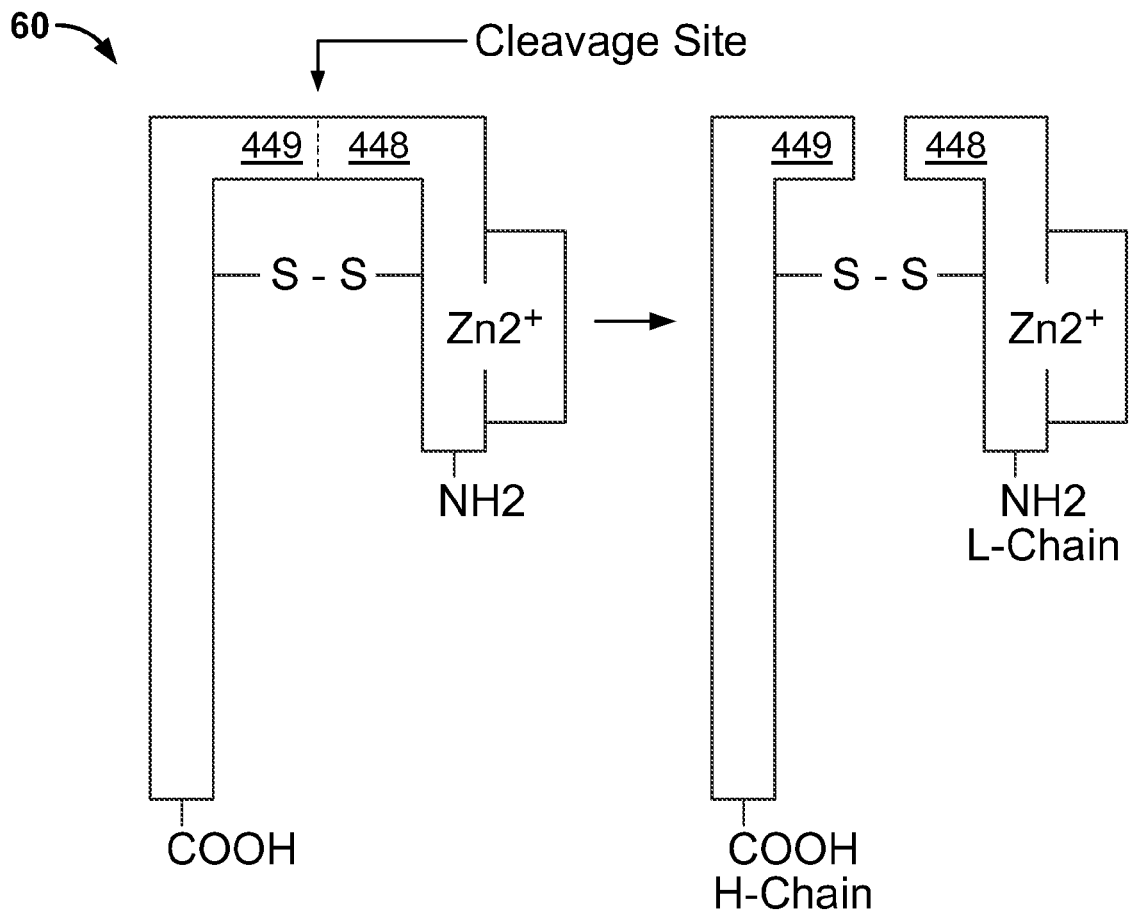
FIG. 6 is a schematic view of a cleaving process of the neurotoxin illustrated in FIG. 4 according to the first embodiment.

As illustrated in FIG. 5, the electro active layer 50 may also comprise a second linking element 90 adapted to bind to the neurotoxin 60. In embodiments, this process functionalizes the neurotoxin 60 or botulinum toxin. This process involves the biotinylation of the neurotoxin 60 or botulinum toxin. Botulinum toxin may be biotinylated through its free sulfhydryl groups that are not essential to its neurotoxicity. This process is described in, for example, Daniels-Holgate et al. (supra). As illustrated in FIG. 6, the botulinum toxin protein can be cleaved at its disulfide bond to free up a sulfhydryl group, which then can be biotinylated. An example of this process is depicted in the following representative reaction:

antibody binding," Biosensors & Bioelectronics, Vol. 20, pp. 260-268 (2004), which are expressly incorporated herein by reference. In embodiments, the bonds may be severed by a current supplied from the voltage source to compel iontophoretic transfer of the neurotoxin into target tissues.

The current may further cause electroporation of a membrane of the target location 25 to enhance delivery of the neurotoxin into target tissues of the target location 25, as described in the '603 application. In addition to the '603 application, electroporation is further described in, for example, Dean, "Electroporation of the Vasculature and the Lung," DNA and Cell Biology, Vol. 22, No. 12, pp. 797-806 (2003); Yang, "Imaging of Vascular Gene Therapy," Radiology, Vol. 228, pp. 36-49 (2003); Duncan, "The Dawning Era of Polymer Therapeutics," Nature Reviews, Vol. 2, pp. 347-360 (2003); and Lavasanifar et al., "Poly(ethylene oxide)-block-poly(L-amino acid) micelles for drug delivery," Advanced Drug Delivery Reviews, Vol. 54, pp. 169-190 (2002). These publications are expressly incorporated herein by reference.

This invention further contemplates the use of derivatives and/or analogs of biotin, as would be understood by one of ordinary skill in the art.

Referring back to FIG. 5, the electroactive layer 50 also may comprise a bridging element 100 adapted to form a first bond to the first linking element 80 and a second bond to the second linking element 90 simultaneously, thereby forming a bridge to connect the electroactive polymer matrix 55 and the neurotoxin 60. In this embodiment, the bridging element 100 is avidin. Avidin is capable of binding four biotins by non-covalent interaction that is quasi-irreversible due to the high affinity of the avidin-biotin bridge. Formation of an avidin-biotin bridge with biotinylated proteins has been described in, for example, Cosnier et al., "Fabrication of biosensors by attachment of biological macromolecules to electropolymerized conducting films," Analusis, Vol. 27, pp. 558-563 (1999) and Dupont-Filliard et al., "Comparison by QCM and photometric enzymatic test of the biotin-avidin recognition on a biotinylated polypyrrole," Talanta, Vol. 55, pp. 981-992 (2001). These publications are expressly incorporated herein by reference.

This invention further contemplates the use of derivatives and/or analogs of avidin, as would be understood by one of ordinary skill in the art.

Figure 7:
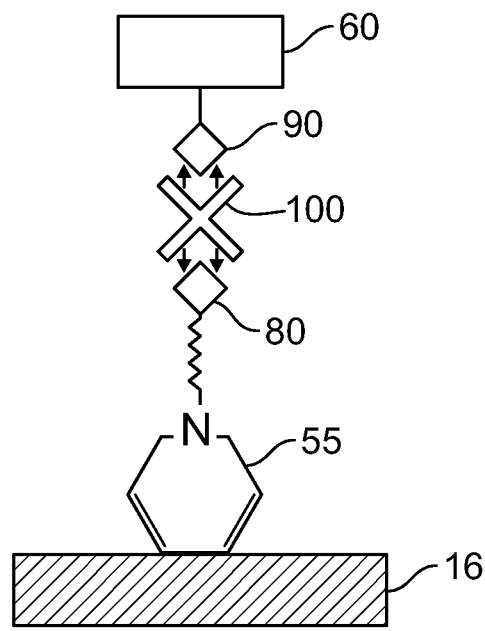
FIG. 7 is a schematic view of the electroactive layer illustrated in FIG. 5 during iontophoresis.

As illustrated in FIG. 7, the bonds between the first linking element 80 and the bridging element 100 and the second linking element 90 and the bridging element 100 may be released by any suitable method. The release of molecules from polypyrrole surfaces is described generally in, for example, Dupont-Filliard et al., "Reversible oligonucleotide immobilisation based on biotinylated polypyrrole film," Analytica Chimica Acta, Vol. 449, Issues 1-2, pp. 45-50 (2001) and Gooding et al., "Electrochemical modulation of antigen- In embodiments, as described in the '603 application, the voltage pulses for electroporation may have a field strength of 50-500 V/cm, more typically 100-200 V/cm, among other ranges, and may have a duration that may vary widely, commonly ranging, for example, between 0.0001 ms and 10,000 ms, among other ranges. Single and multiple pulses are commonly employed, with 5 to 20 pulses (e.g., 10 pulses) being typical.

The electrochemical layer 50 also may comprise additional therapeutic agents, such as, for example, an anti-restenotic agent. Various therapeutic agents are contemplated and are within the spirit and scope of the invention. The therapeutic agent will be dependent upon the condition treated. For example, for the treatment of restenosis, paclitaxel may be used as the therapeutic agent. A number of suitable therapeutic agents that may be used with the invention are known in the art. For example, therapeutic agents that may be used with the invention are disclosed in U.S. Patent Application Publication No. 2008/0107794 to O'Connor et al., the disclosure of which is expressly incorporated herein by reference.

Figure 8:
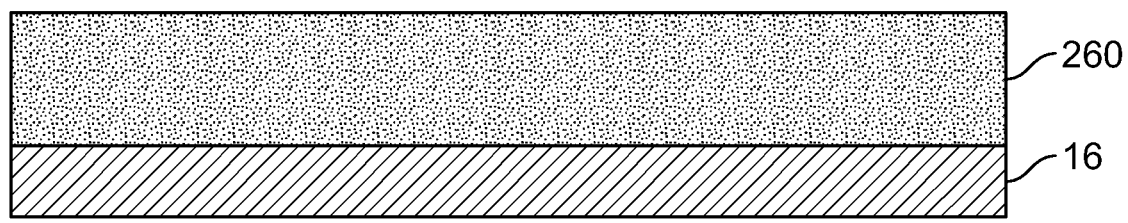
FIG. 8 is a cross-sectional view of an electrode region of the therapeutic agent delivery device illustrated in FIG. 1 according to another embodiment.

As illustrated in FIG. 8, a therapeutic agent delivery device according to a another embodiment comprises a neurotoxin 260 formed directly on the surface of the first conducting element 16. In this embodiment, the second conducting element 17 may be placed in the target location 25 or outside the lumen to complete the electrical circuit, as would be understood by one of ordinary skill in the art. In this embodiment, the neurotoxin 260 forms a self-assembled monolayer on the surface of the first conducting element 16.

Figure 9:
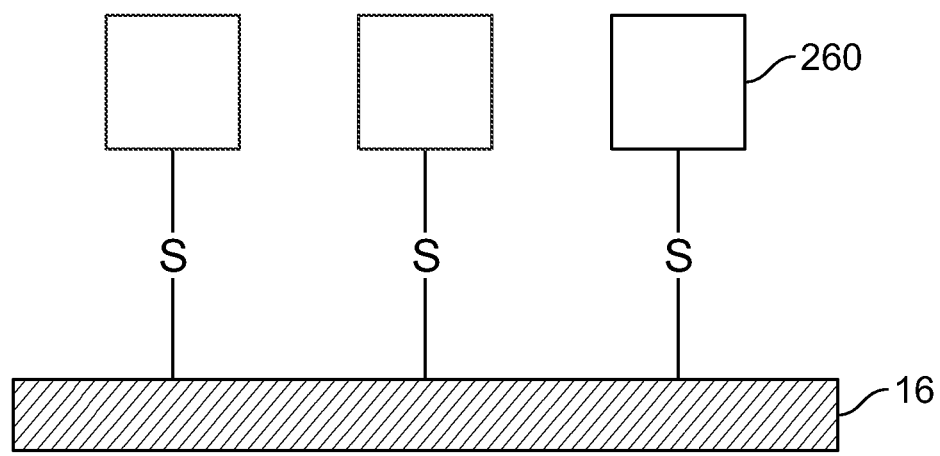
FIG. 9 is a schematic view of the electrode region of the embodiment illustrated in FIG. 8.

For purposes of this disclosure, this embodiment will be described with respect to the first conducting element 16 formed from gold (Au). The formation of self-assembled monolayers is documented in, for example, Wrobel et al., "Covalent immobilization of oligonucleotides on electrodes," Colloids and Surfaces, Vol. 32, pp. 157-162 (2003), which is expressly incorporated herein by reference. Referring back to FIG. 6, cleaving the botulinum toxin frees a sulfhydryl group. Application of controlled electrical current allows the sulfhydryl groups to bind to the Au surface of the first conducting element through a process known in the art as active adsorption as described in, for example, Ozoemena et al., "Voltammetric characterization of the self-assembled monolayer (SAM) of octabutylthiophthalocyaninatoiron(II): a potential electrochemical sensor," Electrochimica Acta, Vol. 47, pp. 4035-4043 (2002), which is expressly incorporated herein by reference. The following representative graphic depicts an example of sulfide bonding and growth of a protein element to a metallic surface indicative of the botulinum sulfide bonding of this embodiment:

reductive desorption. Reductive desorption is a process by which negative potentials reduce the bond, as illustrated in FIG. 9, between the sulfhydryl group and the Au surface, thereby liberating the neurotoxin 260 from the first conductive element 16. Reductive desorption is described in, for example, Wackerbarth et al., "Thiol- and disulfide-modified oligonucleotide monolayer structures on polycrystalline and single-crystal Au(111) surfaces," Journal of Solid State Electrochemistry, Vol. 8, pp. 474-481 (2004) and Buoninsegni et al., "Total and free charge densities on coated self-assembled phosphatidylcholine and octadecanethiol monolayers and octadecanethiol/phosphatidylcholine bilayers," Journal of Solid State Electrochemistry, Vol. 500, pp. 395-407 (2001). These publications are incorporated herein by reference. The current may further cause electroporation of a membrane of the target location to enhance delivery of the neurotoxin into target tissues.

In embodiments, the voltage source for supplying a current to the electrode regions 15 may be, for example, a low voltage battery which will generate DC current through the first and second conductive elements 16, 17. The source of electrical potential for use in connection with the present invention can be quite simple, consisting, for example, of a DC battery and an on/off switch. Alternatively, more complex systems can be utilized. For example, an electrical link may be established with a microprocessor, allowing a complex set of control signals to be sent to the electroactive polymer matrix. These FIG. 9 illustrates the neurotoxin 260 formed in a self-assembled monolayer on the first conductive element according to this embodiment.

In this embodiment, when the electrode regions are connected to the voltage source, a current transfers the neurotoxin 260 to a target location by a process known in the art as more complex systems may be used, for example, where multiple active members are used to exert complex dimensional changes.

In certain embodiments, the electrode regions 15 may be cutting members, blades or microneedles coupled in a suitable manner to expandable member 30. These elements may serve to cut, puncture or otherwise facilitate the movement of the neurotoxin to the target location 25.

A variety of other penetrating members may be used in the present invention. Other examples of penetrating members include tubular protrusions such as those described in U.S. Pat. No. 6,210,392 to Vigil et al., which is incorporated herein by reference in its entirety.

The operation of the embodiments of FIGS. 1-7 and 8-9, will now be described with respect to a method of using the therapeutic agent delivery device 10. For explanatory purposes only, this embodiment will be described with reference to restenosis of a coronary artery. One of ordinary skill in the art will readily recognize that the therapeutic agent delivery device 10 may be used in other suitable applications.

In the embodiments of FIGS. 1-7, prior to use, the electroactive layer 50 is developed according to procedures known in the art, for example, by electrochemical deposition. The use of these electrochemical deposition procedures provides the advantage of precisely electrogenerating a polymer coating over conductive surfaces, such as electrode regions 15, even given the complex geometry of surfaces of certain medical devices, and of exact control of the thickness of the layer based on the amount of electrical current passed during the formation of the electropolymerizable layer as described in Cosnier et al., Analusis (supra). In this manner, an electroactive layer 50, including the desired amount of neurotoxin 60, is selectively grown on the surface of the first and second conductive elements 16, 17 by controlling the current applied through elements 16, 17.

In the embodiments of FIGS. 8-9, prior to use, the neurotoxin 260 is assembled on the surface of the first conducting element 16 according to the active adsorption methods known in the art or, for example, as described in Wrobel et al. (supra) and as discussed above.

In practice, a physician, for example, inserts the distal end of the catheter 20 (which is the portion with the therapeutic agent delivery area on the expandable member 30) through, for example, the femoral artery of the patient and guides the therapeutic agent delivery device 10 through the vasculature to the target location 25 in a coronary artery.

In the embodiments of FIGS. 1-7, once the therapeutic agent delivery area is at the target location 25, the first conductive element 16 and the second conductive element 17 of the electrode regions 15 will be connected to the voltage source. The voltage source applies a potential to the first and second conductive elements 16, 17. Consequently, as discussed above, an iontophoretic reaction occurs driving the neurotoxin 60 into the target location 25.

In the embodiments of FIGS. 8-9, after the first conductive element 16 and the second conductive element 17 of the electrode regions 15 are connected to the voltage source, reductive desorption occurs releasing the neurotoxin from the surface of the first conductive element and driving it to the target location 25.

Regeneration of the therapeutic agent delivery device 10 also is within the scope of this invention. By controlling the application of current to the first and second conductive elements 16, 17, the electrical state of the element 16, 17 can be altered such that charged neurotoxin or therapeutic agent can be reassembled on the surfaces of the elements 16, 17.

In the embodiments illustrated in FIGS. 1-9, the electrochemical circuit of the devices and methods described herein provides for acute, controlled delivery of therapeutic agent to a diseased site. In this regard, these embodiments provide for a minimally invasive insertion procedure in which the expandable member 30 is in an unexpanded position to avoid disruption of or damage to the tissue in route to the target location. Once at the target location, the expandable member 30 is expanded. Up until this point, the neurotoxin therapeutic agent is securely bound to the electroactive polymer matrix 55 or first conductive surface 16 by the either the strong biotin-avidin-biotin bridge or the sulfide bonds of the botulinum toxin. Unlike conventional methods and devices, the neurotoxin therapeutic agent remains adhered to these surfaces so as to be protected from foreign particles in the blood stream or tissue that may dissolve or react with the neurotoxin or therapeutic agent until the physician has positioned the therapeutic agent delivery device 10 at the desired location.

Prior to insertion, the manufacturer and/or physician is able to control the location and amount of neurotoxin applied to the surface of the expandable member 30. After insertion, the physician is then able to control the amount and rate of application of the neurotoxin or therapeutic agent via the electroactive layer 50 to the target location 25 by manipulating the voltage source driving the electrochemical reactions. The result is that improved application and minimized loss of the therapeutic agent to that location can be obtained, producing significantly lower overall costs and improved performance of the device over conventional devices and methods.

Disclosed embodiments have been described with reference to several exemplary embodiments. There are many modifications of the disclosed embodiments which will be apparent to those of skill in the art. It is understood that these modifications are within the teaching of the present invention which is to be limited only by the claims.

What is claimed is:

1. A method of delivering a therapeutic agent to a target location, the method comprising:
   (a) using a therapeutic agent delivery device comprising:
      (i) a conductive element; and
      (ii) an electrochemical layer including an electroactive polymer matrix, a neurotoxin, a first linking element adapted to bind to the electroactive polymer matrix, a second linking element adapted to bind to the neurotoxin, and a bridging element adapted to form a first bond to the first linking element and a second bond to the second linking element, thereby forming a bridge to connect the electroactive polymer matrix and the neurotoxin;
   wherein the conductive element is adapted to be connected to a voltage source;
   (b) positioning a therapeutic agent delivery area of the therapeutic agent delivery device at a target location; and
   (c) connecting the conductive element to the voltage source, thereby causing an electrochemical reaction resulting in at least one of the first bond and the second bond being severed, thereby causing the neurotoxin to release from the therapeutic agent delivery device and elute to a target location.

2. The method of delivering a therapeutic agent according to claim 1, wherein the step of positioning the therapeutic agent delivery area of the device at a target location comprises positioning the therapeutic agent delivery area of the device at a target location in a blood vessel.

3. The method of delivering a therapeutic agent according to claim 1, wherein the release of the neurotoxin causes a flaccid paralysis in the vascular smooth muscle tissue.

4. The method of delivering a therapeutic agent according to claim 1, wherein the therapeutic agent delivery device further comprises:
   a second conductive element adapted to be connected to the voltage source;

wherein the electrochemical layer is located between the first conductive element and the second conductive element.

5. The method of delivering a therapeutic agent according to claim 4, wherein the step of connecting the first conductive element to the voltage source also comprises connecting the second conductive element to the voltage source, causing the electrochemical reaction that causes the neurotoxin to release from the electrochemical layer and elute to a target location.

6. The method of delivering a therapeutic agent according to claim 1, wherein the neurotoxin is selected from the group consisting of botulinum toxins, derivatives thereof, analogs thereof, and botulinum producing cultures.

7. A method of delivering a therapeutic agent to a target location, the method comprising:
(a) using a therapeutic agent delivery device, the therapeutic agent delivery device comprising:
a first conductive element;
a second conductive element; and
an electroactive layer including a neurotoxin located between the first conductive element and the second conductive element, wherein the electroactive layer includes an electroactive polymer matrix, a first linking element adapted to bind to the electroactive polymer matrix, a second linking element adapted to bind to the neurotoxin, and a bridging element adapted to form a first bond to the first linking element and a second bond to the second linking element, thereby forming a bridge to connect the electroactive polymer matrix and the neurotoxin;
wherein the first conductive element and the second conductive element are adapted to be connected to a voltage source; and
(b) connecting the first conductive element and the second conductive element to the voltage source, thereby causing an electrochemical reaction to occur, resulting in at least one of the first bond and the second bond being severed, which in turn causes the neurotoxin to release from the electroactive layer and elute to a target location.

8. The method of delivering a therapeutic agent according to claim 7, wherein the electroactive polymer matrix comprises a polymer selected from the group consisting of a polypyrrole, a polyaniline and a polyamide.

9. The method of delivering a therapeutic agent according to claim 7, wherein the first linking element and second linking element comprise biotin, derivatives thereof, or analogs thereof.

10. The method of delivering a therapeutic agent according to claim 7, wherein the bridging element comprises avidin, derivatives thereof, or analogs thereof.

11. The method of delivering a therapeutic agent according to claim 7, wherein the neurotoxin is selected from the group consisting of botulinum toxins, derivatives thereof, analogs thereof, and botulinum producing cultures.

12. The method of delivering a therapeutic agent according to claim 7, wherein the electroactive layer further comprises an additional therapeutic agent.

13. The method of delivering a therapeutic agent according to claim 7, wherein the therapeutic agent delivery device comprises a balloon.

* * * * *